(12) United States Patent
Cappelleri

(10) Patent No.: US 12,715,111 B2
(45) Date of Patent: Aug. 25, 2026

(54) MICROROBOT CONTROL SYSTEM AND METHOD

(71) Applicant: Purdue Research Foundation, West Lafayette, IN (US)

(72) Inventor: David John Cappelleri, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 37 days.

(21) Appl. No.: 18/897,322

(22) Filed: Sep. 26, 2024

(65) Prior Publication Data

US 2025/0100129 A1 Mar. 27, 2025

Related U.S. Application Data

(60) Provisional application No. 63/540,769, filed on Sep. 27, 2023.

(51) Int. Cl.
*B25J 9/02* (2006.01)
*A61B 8/00* (2006.01)
(Continued)

(52) U.S. Cl.
CPC ............. *B25J 9/026* (2013.01); *A61B 8/4494* (2013.01); *B25J 9/161* (2013.01); *B25J 9/1664* (2013.01); *B25J 19/04* (2013.01)

(58) Field of Classification Search
CPC . B25J 9/026; B25J 9/161; B25J 9/1664; B25J 19/04; A61B 8/449
See application file for complete search history.

(56) References Cited

U.S. PATENT DOCUMENTS 4,934,365 A * 6/1990 Morgenthaler ........ A61N 1/403 607/101
6,091,995 A * 7/2000 Ingle ...................... A61N 1/403 606/41
(Continued)

FOREIGN PATENT DOCUMENTS

CN 102232836 A * 11/2011 ........... A61B 6/0487
CN 102389364 A * 3/2012
(Continued)

OTHER PUBLICATIONS

"Image-Integrated Magnetic Actuation Systems for Localization and Remote Actuation of Medical Miniature Robots: A Survey;" Du et al., IEEE Transactions on Robotics (vol. 39, Issue: 4, 2023, pp. 2549-2568); Aug. 1, 2023. (Year: 2023).*
(Continued)

*Primary Examiner* — Khoi H Tran
*Assistant Examiner* — Jorge O Peche
(74) *Attorney, Agent, or Firm* — Purdue Research Foundation

(57) ABSTRACT

The robot control system configured to control a robot includes a gantry frame having an x-axis guide, a y-axis guide, a first arm, and a second arm. The y-axis guide is coupled to the x-axis guide. The y-axis guide is selectively movable along an x-axis of the x-axis guide. Each of the first arm and the second arm are coupled to the y-axis guide. Each of the first arm and the second arm are independently movable along a y-axis of the y-axis guide. The first arm and/or the second arm are independently movable along a z-axis. A magnet device is coupled to the first arm. An imaging device is coupled to the second arm.

20 Claims, 4 Drawing Sheets

(51) Int. Cl.

| | |
|---|---|
| ***B25J 9/16*** | (2006.01) |
| ***B25J 19/04*** | (2006.01) |

(56) References Cited

U.S. PATENT DOCUMENTS

| | | | | |
|---|---|---|---|---|
| 6,325,758 | B1 * | 12/2001 | Carol | A61N 5/1049 128/916 |
| 6,330,467 | B1 * | 12/2001 | Creighton, IV | A61B 1/00158 600/407 |
| 9,579,088 | B2 * | 2/2017 | Farritor | A61B 34/74 |
| 10,687,909 | B2 * | 6/2020 | Noonan | A61B 90/37 |
| 11,324,554 | B2 * | 5/2022 | Lee | A61B 34/20 |
| 11,646,632 | B2 * | 5/2023 | Takata | H02K 7/1025 318/742 |
| 12,089,907 | B2 * | 9/2024 | Mantri | A61B 34/25 |
| 12,269,158 | B2 * | 4/2025 | Chen | B25J 19/0075 |
| 2002/0090058 | A1 * | 7/2002 | Yasuda | A61B 6/4464 378/205 |
| 2003/0125622 | A1 * | 7/2003 | Schweikard | A61B 90/10 600/437 |
| 2004/0111183 | A1 * | 6/2004 | Sutherland | A61B 34/76 700/245 |
| 2005/0020917 | A1 * | 1/2005 | Scherch | A61N 5/1049 600/437 |
| 2007/0015991 | A1 * | 1/2007 | Fu | A61N 5/1049 600/407 |
| 2007/0078327 | A1 * | 4/2007 | Kindlein | A61N 5/1007 600/407 |
| 2008/0308611 | A1 * | 12/2008 | Alessi | B23K 20/1205 228/2.1 |
| 2009/0005677 | A1 * | 1/2009 | Weber | A61B 6/547 600/426 |
| 2011/0213247 | A1 * | 9/2011 | Shammas | A61B 8/4218 367/99 |
| 2011/0230894 | A1 * | 9/2011 | Simaan | A61B 1/05 606/130 |
| 2011/0237890 | A1 * | 9/2011 | Farritor | A61B 34/30 600/142 |
| 2011/0257661 | A1 * | 10/2011 | Choi | A61B 1/00094 606/130 |
| 2012/0022552 | A1 * | 1/2012 | Neff | A61B 34/30 606/130 |
| 2012/0099697 | A1 * | 4/2012 | Helm | A61B 6/50 378/4 |
| 2012/0289821 | A1 * | 11/2012 | Graumann | A61B 6/4441 378/19 |
| 2013/0090764 | A1 * | 4/2013 | Summer | B25J 3/00 901/1 |
| 2013/0289579 | A1 * | 10/2013 | Yeung | A61B 34/30 606/130 |
| 2013/0289581 | A1 * | 10/2013 | Yeung | A61B 34/73 606/130 |
| 2013/0289768 | A1 * | 10/2013 | Yeung | A61B 34/73 700/258 |
| 2013/0335085 | A1 * | 12/2013 | Arimitsu | H02N 2/163 324/318 |
| 2014/0058407 | A1 * | 2/2014 | Tsekos | A61B 34/30 606/130 |
| 2014/0180115 | A1 * | 6/2014 | Tsuruno | A61B 8/4461 600/459 |
| 2014/0303644 | A1 * | 10/2014 | Choi | A61B 34/30 606/130 |
| 2015/0051517 | A1 * | 2/2015 | Vahala | A61B 5/055 601/3 |
| 2015/0230810 | A1 * | 8/2015 | Creighton | A61K 41/0028 604/518 |
| 2015/0297177 | A1 * | 10/2015 | Boctor | A61B 34/30 901/47 |
| 2016/0157882 | A1 * | 6/2016 | Oila | A61N 7/02 606/169 |
| 2017/0200271 | A1 * | 7/2017 | Atria | A61B 6/032 |
| 2018/0085926 | A1 * | 3/2018 | Kogan | B25J 19/023 |
| 2018/0242929 | A1 * | 8/2018 | Yano | A61B 6/0487 |
| 2018/0243149 | A1 * | 8/2018 | Yano | A61G 13/04 |
| 2019/0000560 | A1 * | 1/2019 | Berman | A61B 34/20 |
| 2019/0099141 | A1 * | 4/2019 | Garlow | A61B 6/4405 |
| 2019/0117999 | A1 * | 4/2019 | Fontanarosa | A61N 5/1049 |
| 2019/0261846 | A1 * | 8/2019 | Oh | A61B 1/015 |
| 2020/0008874 | A1 * | 1/2020 | Barbagli | A61B 34/10 |
| 2020/0015924 | A1 * | 1/2020 | Scheib | G01S 17/36 |
| 2020/0170730 | A1 * | 6/2020 | Cameron | A61B 34/30 |
| 2020/0246088 | A1 * | 8/2020 | Mewes | A61B 6/12 |
| 2020/0261297 | A1 * | 8/2020 | Strydom | A61G 13/0081 |
| 2020/0405403 | A1 * | 12/2020 | Shelton, IV | A61B 17/3421 |
| 2021/0059779 | A1 * | 3/2021 | Zhao | A61B 34/30 |
| 2021/0146551 | A1 * | 5/2021 | Huang | G01B 7/004 |
| 2021/0290311 | A1 * | 9/2021 | Fuerst | B25J 19/027 |
| 2021/0322020 | A1 * | 10/2021 | Shelton, IV | H04L 67/10 |
| 2021/0369373 | A1 * | 12/2021 | Zhang | A61B 34/30 |
| 2022/0029510 | A1 * | 1/2022 | Takeshima | H02K 15/03 |
| 2022/0061927 | A1 * | 3/2022 | Sramek | A61B 34/20 |
| 2022/0074088 | A1 * | 3/2022 | Vicerial | D03D 25/00 |
| 2022/0110691 | A1 * | 4/2022 | Govari | A61B 34/70 |
| 2022/0122752 | A1 * | 4/2022 | Jang | A61B 34/35 |
| 2022/0143817 | A1 * | 5/2022 | Marvi | B25J 9/161 |
| 2022/0272272 | A1 * | 8/2022 | Keenan | H04N 23/66 |
| 2022/0341217 | A1 * | 10/2022 | Cristache | G06N 5/02 |
| 2022/0360723 | A1 * | 11/2022 | Fujii | A61B 1/00055 |
| 2023/0054209 | A1 * | 2/2023 | Roh | A61B 34/76 |
| 2023/0106912 | A1 * | 4/2023 | Kumar | A61B 34/30 600/411 |
| 2023/0191630 | A1 * | 6/2023 | Norton | B25J 18/00 74/490.01 |
| 2023/0210604 | A1 * | 7/2023 | Berman | A61B 6/4441 378/177 |
| 2023/0355194 | A1 * | 11/2023 | Gregerson | A61B 6/035 |
| 2024/0065777 | A1 * | 2/2024 | Gregerson | A61B 90/39 |
| 2024/0341881 | A1 * | 10/2024 | Helm | A61B 8/40 |
| 2024/0382265 | A1 * | 11/2024 | Kemp | A61B 90/39 |
| 2024/0415671 | A1 * | 12/2024 | Blachon | A61B 34/10 |
| 2025/0100129 | A1 * | 3/2025 | Cappelleri | A61B 8/4494 |
| 2025/0160971 | A1 * | 5/2025 | Shelton, IV | G16H 40/63 |
| 2025/0235277 | A1 * | 7/2025 | Avisar | A61B 34/70 |
| 2025/0319596 | A1 * | 10/2025 | Nilsson | A61B 34/30 |

FOREIGN PATENT DOCUMENTS

| | | | | | |
|---|---|---|---|---|---|
| CN | 103582462 | A | * | 2/2014 | A61B 34/73 |
| CN | 104729401 | A | * | 6/2015 | |
| CN | 205673935 | U | * | 11/2016 | |
| CN | 109862845 | B | * | 12/2022 | B25J 9/0018 |
| CN | 116236288 | A | * | 6/2023 | B25J 9/1679 |
| CN | 116711017 | A | * | 9/2023 | G16H 20/70 |
| EP | 3471622 | B1 | * | 10/2023 | A61B 8/467 |
| EP | 4296203 | A1 | * | 12/2023 | B65G 1/1375 |
| KR | 101720032 | B1 | * | 3/2017 | A61G 13/02 |
| KR | 20190043778 | A | * | 4/2019 | A61G 13/10 |
| WO | WO-2008020834 | A1 | * | 2/2008 | A61B 90/50 |
| WO | WO-2009036785 | A1 | * | 3/2009 | B28D 1/043 |
| WO | WO-2014015421 | A1 | * | 1/2014 | A61B 5/055 |
| WO | WO-2017098699 | A1 | * | 6/2017 | B25J 9/1664 |
| WO | WO-2022060793 | A1 | * | 3/2022 | A61B 6/027 |

OTHER PUBLICATIONS

"Remote Control of Untethered Magnetic Robots within a Lumen using X-Ray-Guided Robotic Platform;" Ligtenberg et al., 2024 IEEE International Conference on Robotics and Automation (ICRA) (2024, pp. 17763-17769); May 13, 2024. (Year: 2024).*

"Enhanced Motion Control of Magnetically Actuated Capsule Robot Using MEMA—A Mobile Electromagnetic Actuation System;" Lee et al., IEEE/ASME Transactions on Mechatronics (vol. 30, Issue: 2, 2025, pp. 933-944); Jan. 10, 2025. (Year: 2025).*

Abbott, J. J., et al.,"Magnetic methods in robotics". Annual Review of Control, Robotics, and Autonomous Systems, 3(1), (2020), pp. 57-90.

Armacost, M., Adair, J., et al., "Accurate and reproducible target navigation with the stereotaxis niobe magnetic navigation system". Journal of Cardiovascular Electrophysiology, 18(s1), (2007), pp. s26-s31.

(56) References Cited

OTHER PUBLICATIONS

Chautems, C., et al. 2020. "Magnetic continuum device with variable stiffness for minimally invasive surgery". Advanced Intelligent Systems, 2(6), p. 1900086.
Heunis, C. M., et al. J.-P. P. d., and Misra, S., "Design and evaluation of a magnetic rotablation catheter for arterial stenosis". IEEE/ASME Transactions on Mechatronics, 27(3), (2022) pp. 1761-1772.
Kummer M. P., et al., "Octomag: An electromagnetic system for 5-dof wireless micromanipulation". IEEE Transactions on Robotics, 26(6), (2010) pp. 1006-1017.
Martin, J. W., Scaglioni, et al., "Enabling the future of colonoscopy with intelligent and autonomous magnetic manipulation". Nature Machine Intelligence, 2(10), (2020) pp. 595-606.
Moya, À., et al., "Innovations in heart rhythm disturbances: Cardiac electrophysiology, arrhythmias, and cardiac pacing". Revista Española de Cardiología (English Edition), 66(2), (2013) pp. 116-123.
Mutlu, S., et al., "Magnetic resonance imaging-compatible optically powered miniature wireless modular lorentz force actuators". Advanced Science, 8(2), (2021) p. 2002948.
Pittiglio G., et al. "Dual-arm control for enhanced magnetic manipulation". In 2020 IEEE/RSJ International Conference on Intelligent Robots and Systems (IROS), (2020) pp. 7211-7218.
Staruch, R., et al. "Localised drug release using mri-controlled focused ultrasound hyperthermia". International Journal of Hyperthermia, 27(2), (2011) pp. 156-171.
Yang, Z., et al., Magnetic actuation systems for miniature robots: A review. Advanced Intelligent Systems, 2(9), (2020) p. 2000082.
Yang, Z., et al., "Magnetically actuated continuum medical robots: A review". Advanced Intelligent Systems, vol. 5, Issue 6, (2023) p. 2200416.

* cited by examiner

MICROROBOT CONTROL SYSTEM AND METHOD

CROSS REFERENCE TO RELATED APPLICATIONS

This application claims the priority benefit of U.S. Provisional Patent application No. 63/540,769, filed Sep. 27, 2023, the contents of which is incorporated herein by reference in its entirety.

GOVERNMENT RIGHTS

This invention was made with government support under TR004239 awarded by the National Institutes of Health. The government has certain rights in the invention.

FIELD

The disclosure generally relates to imaging and actuation systems and, more particularly, to systems configured to control robotic devices.

INTRODUCTION

This section provides background information related to the present disclosure which is not necessarily prior art.

Magnetic fields are a popular choice for manipulating small robots operating inside the human body since they are transparent to the biological tissue and can be accurately controlled in real-time. Known systems provide one robotic arm with a permanent magnet while a different known system includes two robotic arms and two permanent magnets. In another known system, an OctoMag® system consists of 8 electromagnets surrounding a workspace. Furthermore, other known systems include a robotic arm driven electro-magnet system (ARMM) while a DeltaMag™ system uses three parallel mechanism driven mobile electromagnets. For visualization, small-animal magnetic resonance imaging (MRI) scanners have been utilized. All of the known robotic arm mounted systems are expensive, large, and bulky, making them difficult to incorporate into existing hospital operating room configurations and workflows. The electromagnetic based systems suffer from low field strengths and workspace sizes and/or the requirement of large amounts of current, which requires the incorporate of external cooling systems for the coils. A few commercial platforms have started to emerge that use either extremely large permanent magnets or electromagnets attached to robotic arms. These systems are extremely expensive and require the dedicated use of an operating room to house such systems, which can prohibit adoption.

Accordingly, there is a continuing need for a robot control system that may be more easily implemented in hospitals in regard to both size and cost to manufacture. Desirably, the robot control system may be versatile in that it may be applied to a plurality of end use applications.

SUMMARY

In concordance with the present disclosure, a robot control system that may be more easily implemented in hospitals, has surprisingly been discovered. Desirably, the robot control system may adaptable so that it may be applied to a plurality of end use applications.

A robot control system configured to control a robot includes a gantry frame having an x-axis guide, a y-axis guide, a first arm, and a second arm. The y-axis guide is coupled to the x-axis guide. The y-axis guide may be selectively movable along an x-axis of the x-axis guide. Each of the first arm and the second arm may be coupled to the y-axis guide. Each of the first arm and the second arm may be independently movable along a y-axis of the y-axis guide. The first arm and/or the second arm may be independently movable along a z-axis. The gantry frame may also be classified as the XY2Z robotic platform. A magnet device may be coupled to the first arm. An imaging device may be coupled to the second arm. Advantageously, the robot control system may provide a single unit that may enable both imaging and magnetic actuation of the robot. Desirably, the gantry frame may be coupled to an operating table to be more easily integrated and used in hospital operating rooms.

The robot control system may be used in various ways. For instance, the robot control system may be used according to a method. The method may include a step of providing the robot control system having a gantry frame including an x-axis guide, a y-axis guide, a first arm, and a second arm. The y-axis guide may be coupled to the x-axis guide. Each of the first arm and the second arm may be coupled to the y-axis guide. The first arm and/or the second arm may be movable along a z-axis. A magnet device may be coupled to the first arm. An imaging device may be coupled to the second arm. Next, a magnetic field may be applied to the robot via the magnetic device. Afterwards, the method may include a step of imaging the robot via the imaging device.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations and are not intended to limit the scope of the present disclosure.

Figure 3:
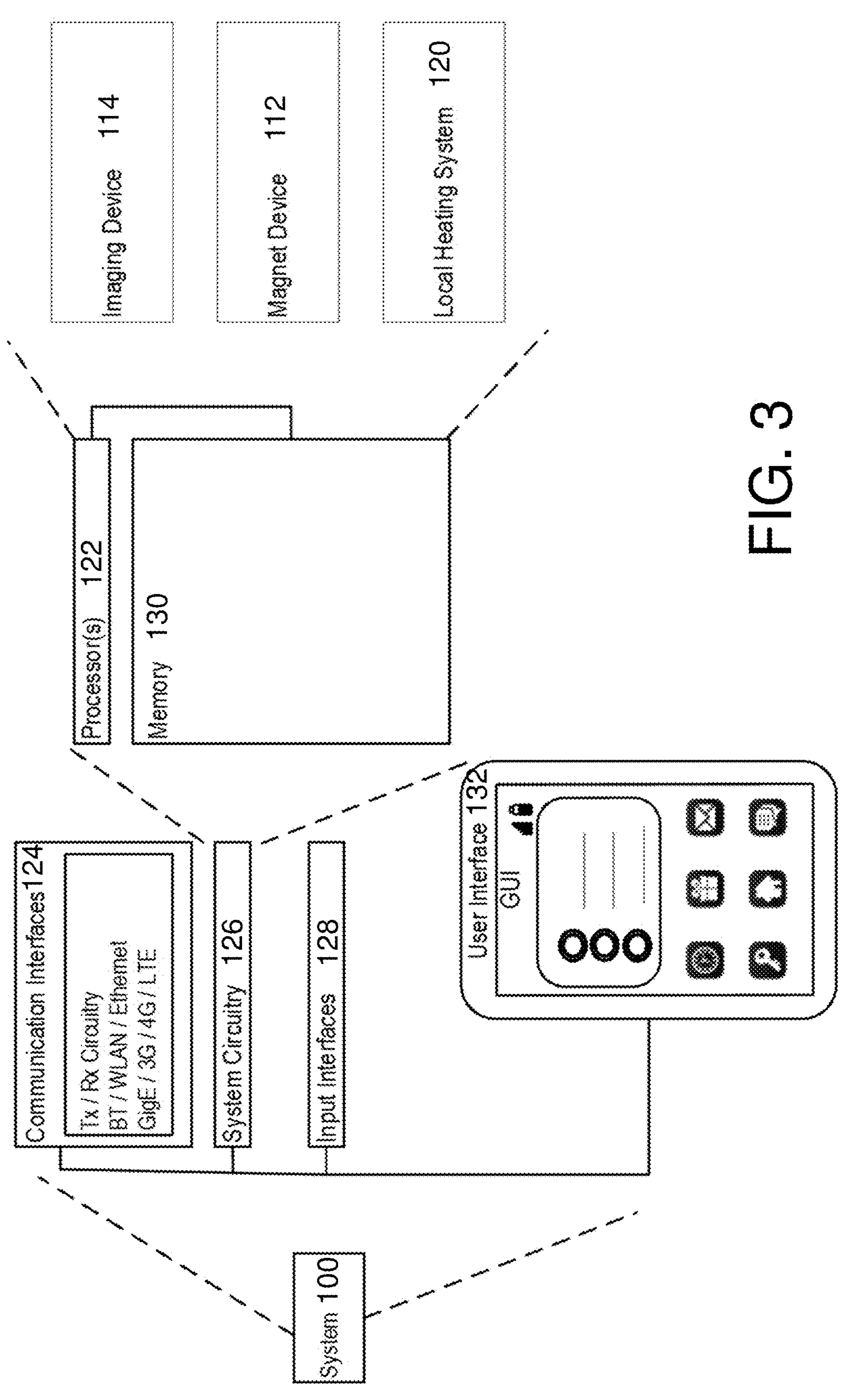
Figure 4:
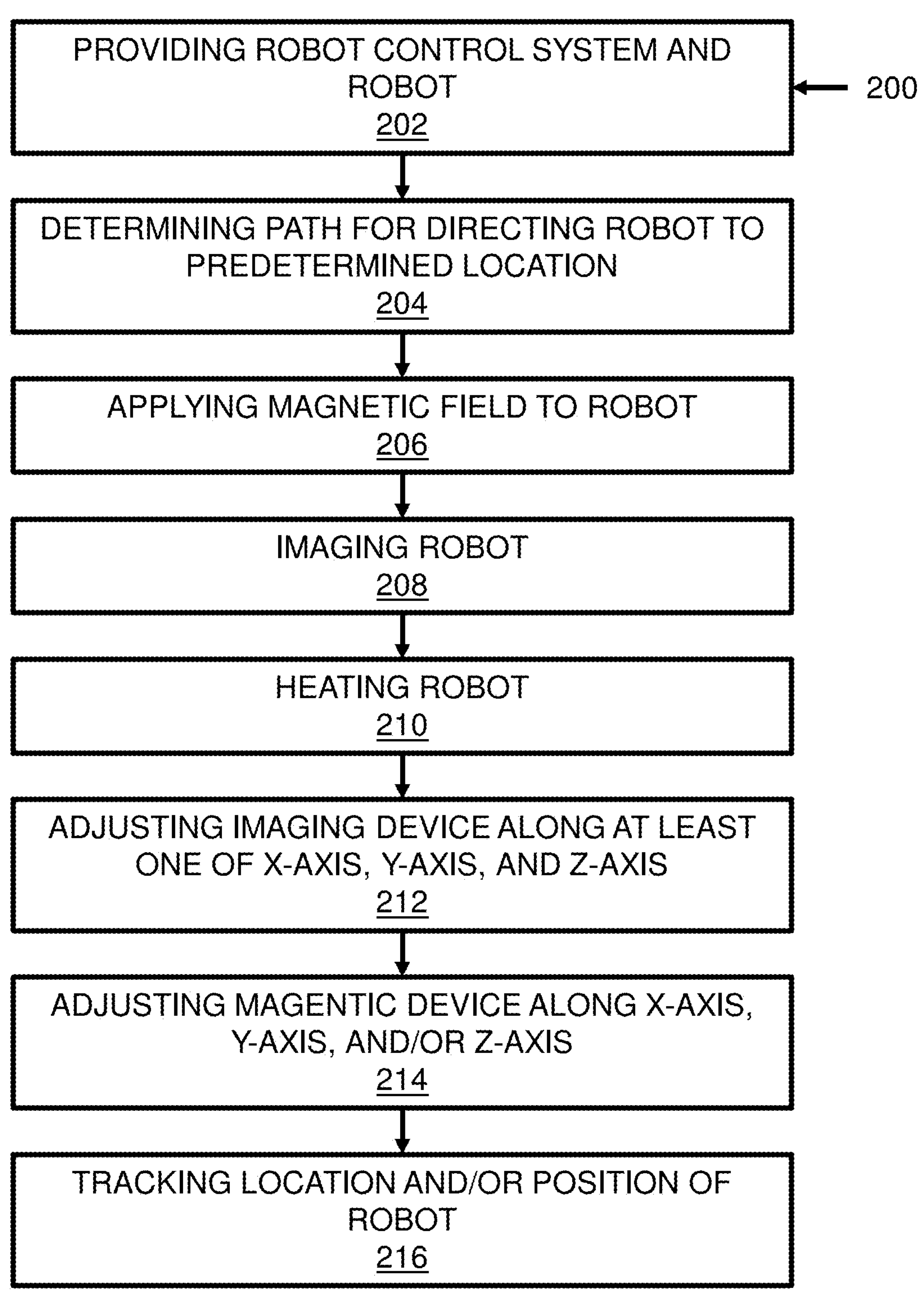

FIG. 3 is a schematic diagram of the system, further depicting the system having a communication interface, an input interface, a user interface, and a system circuitry, wherein the system circuitry may include a processor and a memory, according to one embodiment of the present disclosure; and FIG. 4 is a flow chart of a method for using the robot control system, according to one embodiment of the present disclosure.

DETAILED DESCRIPTION

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. Regarding methods disclosed, the order of the steps presented is exemplary in nature, and thus, the order of the steps can be different in various embodiments, including where certain steps can be simultaneously performed. “A”

and "an" as used herein indicate "at least one" of the item is present; a plurality of such items may be present, when possible. Except where otherwise expressly indicated, all numerical quantities in this description are to be understood as modified by the word "about" and all geometric and spatial descriptors are to be understood as modified by the word "substantially" in describing the broadest scope of the technology. "About" when applied to numerical values indicates that the calculation or the measurement allows some slight imprecision in the value (with some approach to exactness in the value; approximately or reasonably close to the value; nearly). If, for some reason, the imprecision provided by "about" and/or "substantially" is not otherwise understood in the art with this ordinary meaning, then "about" and/or "substantially" as used herein indicates at least variations that may arise from ordinary methods of measuring or using such parameters.

Although the open-ended term "comprising," as a synonym of non-restrictive terms such as including, containing, or having, is used herein to describe and claim embodiments of the present technology, embodiments may alternatively be described using more limiting terms such as "consisting of" or "consisting essentially of." Thus, for any given embodiment reciting materials, components, or process steps, the present technology also specifically includes embodiments consisting of, or consisting essentially of, such materials, components, or process steps excluding additional materials, components or processes (for consisting of) and excluding additional materials, components or processes affecting the significant properties of the embodiment (for consisting essentially of), even though such additional materials, components or processes are not explicitly recited in this application. For example, recitation of a composition or process reciting elements A, B and C specifically envisions embodiments consisting of, and consisting essentially of, A, B and C, excluding an element D that may be recited in the art, even though element D is not explicitly described as being excluded herein.

As referred to herein, disclosures of ranges are, unless specified otherwise, inclusive of endpoints and include all distinct values and further divided ranges within the entire range. Thus, for example, a range of "from A to B" or "from about A to about B" is inclusive of A and of B. Disclosure of values and ranges of values for specific parameters (such as amounts, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that Parameter X may have a range of values from about A to about Z. Similarly, it is envisioned that disclosure of two or more ranges of values for a parameter (whether such ranges are nested, overlapping, or distinct) subsume all possible combination of ranges for the value that might be claimed using endpoints of the disclosed ranges. For example, if Parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, 3-9, and so on.

When an element or layer is referred to as being "on," "engaged to," "connected to," or "coupled to" another element or layer, it may be directly on, engaged, connected, or coupled to the other element or layer, or intervening elements or layers may be present. In contrast, when an element is referred to as being "directly on," "directly engaged to," "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer, or section. Terms such as "first," "second," and other numerical terms when used herein do not imply a sequence or order unless clearly indicated by the context. Thus, a first element, component, region, layer, or section discussed below could be termed a second element, component, region, layer, or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the FIG. is turned over, elements described as "below", or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

Figure 1:
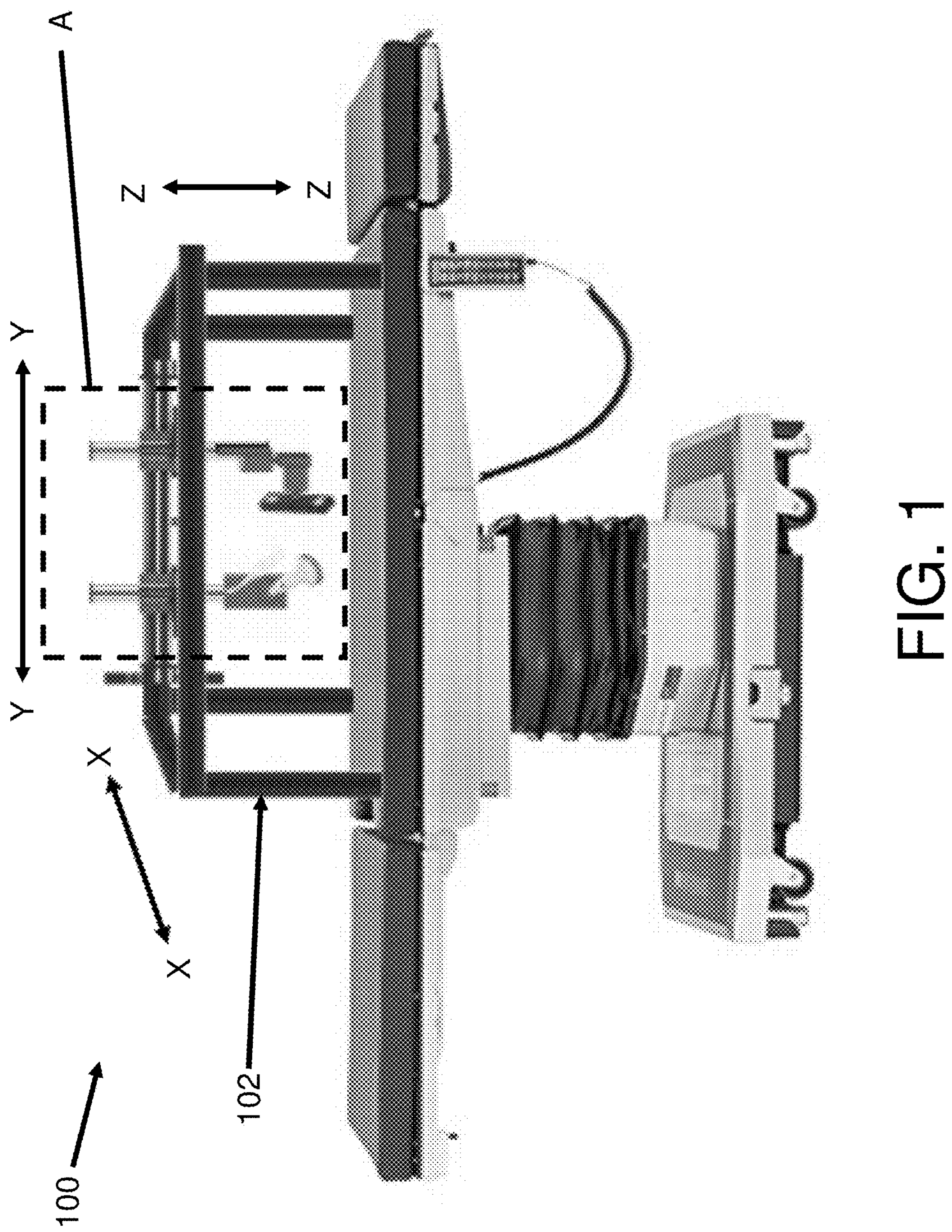
FIG. 1 is a schematic diagram of a robot control system, according to one embodiment of the present disclosure.
Figure 2:
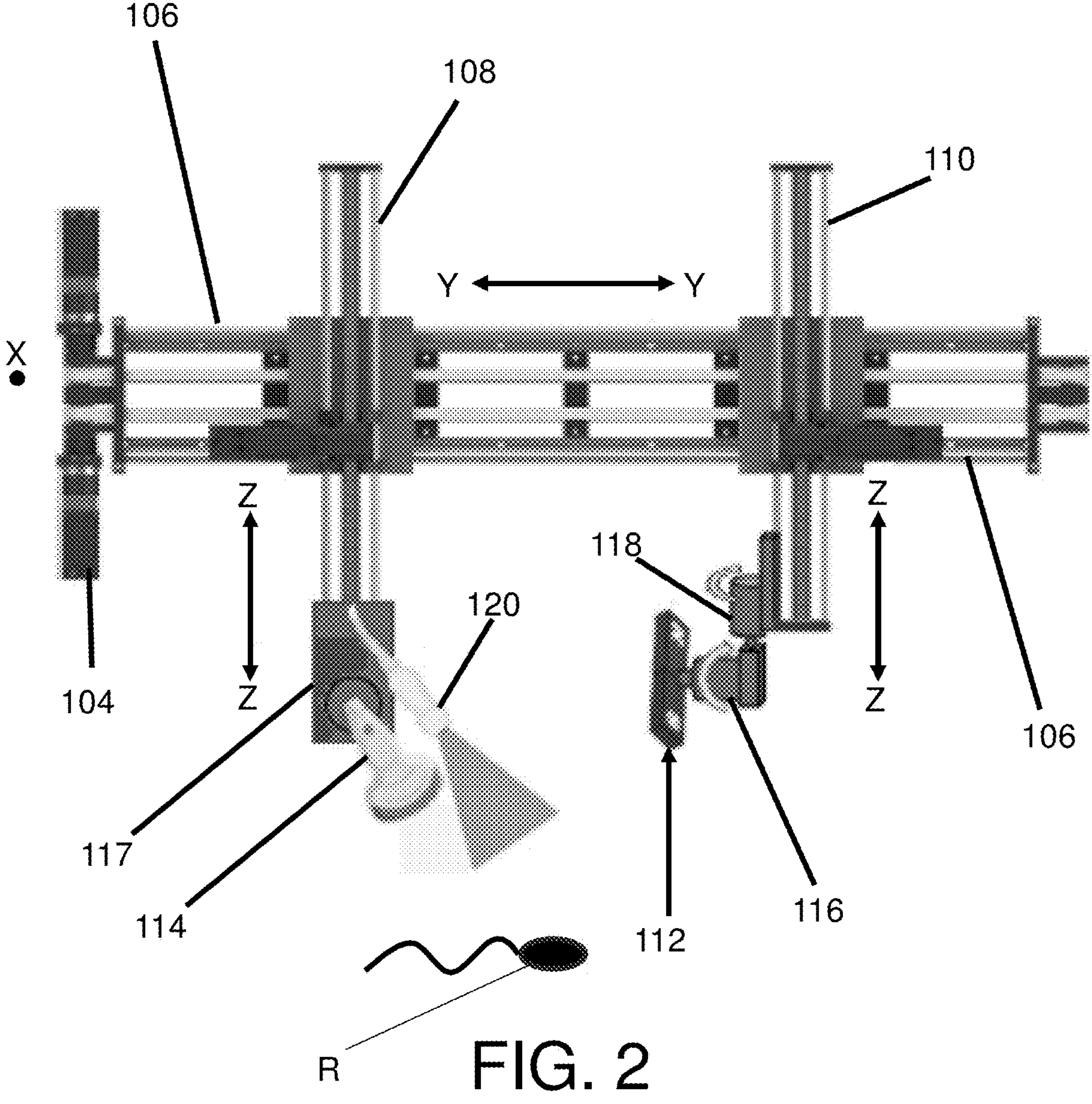
FIG. 2 is an enlarged schematic diagram of the robot control system from call-out A, as shown in FIG. 1, according to one embodiment of the present disclosure.

As shown in FIGS. 1-2, a robot control system 100 configured to control a robot R includes a gantry frame 102 having an x-axis guide 104, a y-axis guide 106, a first arm 108, and a second arm 110. The y-axis guide 106 is coupled to the x-axis guide 104. The y-axis guide 106 may be selectively movable along an x-axis X of the x-axis guide 104. Each of the first arm 108 and the second arm 110 may be coupled to the y-axis guide 106. Each of the first arm 108 and the second arm 110 may be independently movable along a y-axis Y of the y-axis guide 106. The first arm 108 and/or the second arm 110 may be independently movable along a z-axis Z. The gantry frame 102 may also be classified as the XY2Z robotic platform. A magnet device 112 may be coupled to the first arm 108. An imaging device 114 may be coupled to the second arm 110. Advantageously, the robot control system 100 may provide a single unit that may enable both imaging and magnetic actuation of the robot R. Desirably, the gantry frame 102 may be coupled to an operating table to be more easily integrated and used in hospital operating rooms. In a specific example, the robot control system 100 may be removable from the operating table when not in use. For instance, the gantry frame 102 may be selectively coupled to the operating table with clamps, straps, or other such methods that may allow for quickly and securely connecting the gantry frame 102 to the operating table, within the scope of the present disclosure.

In certain circumstances, the magnet device 112 may be provided in various ways. For instance, the magnet device 112 may include a rotating field motor 116 that may rotate a permanent magnet to selectively provide a rotating magnetic field. In other words, the magnet device 112 may include a rotating and steerable permanent magnet for microrobot locomotion. In a more specific example, the magnet device 112 may selectively produce the rotating magnetic field at high operating frequencies (up to around 500 Hz). In another specific example, the magnet device 112 may include a steering motor 118 to direct an axis of the rotating magnetic field. One skilled in the art may select other suitable ways for providing the magnetic device, within the scope of the present disclosure.

In certain circumstances, the imaging device 114 may be provided in various ways. For instance, the imaging device 114 may include an imaging ultrasound transducer. In other words, the imaging device 114 may include an articulated ultrasound imaging transducer for real-time microrobot tracking. In a more specific example, the imaging device 114 may include a linear array ultrasound transducer with a frequency range of around 22 HHz to around 55 HHz and a central frequency of around 40 MHz. The imaging device 114 may produce real-time images of microrobots and its workspace using a B-mode imaging setting. The imaging device 114 may be mounted to a motor for adjusting its orientation. In another specific example, the second arm 110 may include a way to keep the imaging device 114 in contact with a tissue surface of the patient. Force control of the end-effector advantageously may keep the imaging ultrasound transducer in contact with the tissue surface at all times. For instance, the second arm 110 may include a load cell 117 coupled in series with the imaging device 114. The load cell 117 may be configured to measure a contact force between the tissue surface and the second arm 110 and may also keep the imaging device 114 in contact with the tissue surface of the patient. A skilled artisan may select other suitable ways for providing the imaging device 114, within the scope of the present disclosure.

In certain circumstances, the robot control system 100 may include ways to provide heat. For instance, the second arm 110 may include a local heating system 120. More specifically, the local heating system 120 may include a focused ultrasound probe for directed local heating. The ultrasound induced heating may be set to well below the threshold required for tissue damage. For instance, the local heating system 120 may be used for thermal adaptation of microrobots. Provided as a non-limiting example, the local heating system 120 may include a focused low intensity therapeutic ultrasound probe that is highly efficient over a broad bandwidth. It may be directed to a target region where the microrobot R is located with the XY2Z robot. The microrobot R may include various types of microrobots such as helical, rectangular, and spherical robots. The microrobot R may be magnetic, which may then be controlled and moved with the rotating magnetic field. In a specific example, the microrobot R may include a thermally sensitive payload that may be selectively actuated/released when exposed to the engaged local heating system 120. Many different kinds of artificial helical type microrobots have been fabricated in the last twenty years. Some typical fabrication methods of helical swimming microrobots are the self-scrolling method, two-photon polymerization (TPP), glancing angle deposition, and casting. However, these microrobots have bodies made from stiff materials so that the swimming performances are fixed once they are fabricated. Additional functionalities for these microrobots are typically achieved by an additional passive structure or by the motion of the microrobot utilizing the generated flow field. More advanced functionalities are needed to achieve more complex behaviors, such as active micromanipulation, active drug delivery, and adaptive locomotion. The development of smart materials provides a way to realize the above functionalities. Smart materials are able to deform their shapes after fabrication and therefore introduce an additional degree-of-freedom when they are implemented into microrobots. Among those smart materials, hydrogels stand out because of their predominant biocompatibility, which is ideal for biomedical applications. In the past few years, many hydrogels have been used to fabricate microrobots for different purposes, such as microgrippers for object manipulation, microcrawlers for locomotion, and helical microrobots for drug delivery and directing cell chemotaxis. One known photolithographic method fabricates a helical type microrobot with adaptive locomotion capabilities in environments with different viscosities, solute concentrations, and temperatures. Therefore, the use of a local heating system 120 can be used to trigger behaviors in microrobots and small-scale devices that are made from thermally responsive hydrogels or other thermally sensitive materials, greatly increasing the functionality of such robots and devices. A skilled artisan may select other suitable ways for providing heat, within the scope of the present disclosure.

In certain circumstances, the robot control system 100 may be autonomously controlled. For instance, the robot control system 100 may include a processor 122. The processor 122 may be configured to execute the steps of adjusting a rotating magnetic field frequency, $\omega$; adjusting a rotating magnetic field steering angle, $\beta$; adjusting the imaging US tissue contact force, F; adjusting the imaging US orientation angle, $\alpha$; adjusting the focused US local heating intensity, T; and adjusting the positions of each axis of the XY2Z robotic platform, $[X, Y, Z_1, Z_2]$. In a specific example, the processor 122 may autonomously adjust at least one of the imaging device 114 and the magnet device 112 along the x-axis X, the y-axis Y, and the z-axis Z. In another specific example, the processor 122 may autonomously plan a path for directing the robot R to a predetermined location. Further, the processor 122 may autonomously track a position and/or a location of the robot R in real time. One skilled in the art may select other suitable ways for autonomously controlling the robot control system 100, within the scope of the present disclosure. In certain circumstances, the robot control system 100 may autonomously control the behavior of the microrobots R to navigate areas such as the uterus and Fallopian tubes to a desired location.

Provided as a non-limiting example, the following description of values and adjustments may be utilized by the robot control system 100. The appropriate values for F and a may produce a real-time image of the microrobot R. Image processing may be used to determine the current state, s, of the microrobot R corresponding to its position and heading in the workspace. Additionally, the velocity, v, of the microrobot R may be extracted from consecutive time-stamped images. At time instance i, based on the current values for $s_i$, $v_i$, and the desired trajectory waypoint, $wp_k$, the control system may calculate the desired values for the new microrobot state, $s_{i+1}$, and velocity, $v_{i+1}$. It may then update the settings for T, $\omega$, $\alpha$, $\beta$, and $[X, Y, Z_1, Z_2]$ accordingly. Specifically, the value for $F_i$ will be used to determine the update of the vertical position and orientation of the US imaging transducer ($Z_{2(i+1)}$, and $\alpha_{i+1}$), respectively. This contact force value, F, may need to be maintained over a set force threshold at all times in order to provide clear images of the microrobot R and the workspace. The microrobot velocity value, $v_i$, may be used to calculate appropriate adjustments to either or both the rotational magnetic field frequency, $\omega_{i+1}$, and focused US local heating settings, $T_{i+1}$. From system calibration data, the v/ω ratio may be correlated to an efficiency swimming metric, η, in the fluids with a particular viscosity along with nominal velocity values determined for effective image-based tracking. When significant deviation from this target ratio is observed, the T settings may be adjusted to adapt the microrobot R for efficient swimming at a desired velocity. A comparison between the microrobot state $s_i$ and its desired waypoint $wp_k$ to control the magnetic field steering angle β1+1 and the vertical position Z1(*i*+1) of the permanent magnet. The [X, Y] positions of the XY2Z robot R will be updated accordingly to adjust the US field of view and magnetic field workspace. This will be done automatically, to keep the position of the microrobot R and desired waypoint in the imaging US field of view at all times. Without being bound to any particular theory, it is believed that PID control laws will be sufficient for operating each of the control loops of system. It is also contemplated that more sophisticated control techniques, such as adaptive control, may be utilized, within the scope of the present disclosure.

In certain circumstances, as shown in FIG. 3, the robot control system 100 may further include a communication interface 124, a system circuitry 126, and/or an input interface 128. The system circuitry 126 may include the processor 122 or multiple processors. The processor 122 or multiple processors may execute the steps to adjust the y-axis guide 106 along the x-axis X, adjust the first arm 108 and/or the second arm 110 along the y-axis Y, adjust the imaging device 114 and/or the magnet device 112 along the z-axis Z, engaging the imaging device 114, actuating the magnet device 112, and engaging the local heating system 120. Alternatively, or in addition, the system circuitry 126 may include memory 130.

The processor 122 may be in communication with the memory 130. In some examples, the processor 122 may also be in communication with additional elements, such as the communication interfaces 124, the input interfaces 128, and/or a user interface 132. Examples of the processor 122 may include a general processor, a central processing unit, logical CPUs/arrays, a microcontroller, a server, an application specific integrated circuit (ASIC), a digital signal processor, a field programmable gate array (FPGA), and/or a digital circuit, analog circuit, or some combination thereof.

The processor 122 may be one or more devices operable to execute logic. The logic may include computer executable instructions or computer code stored in the memory 130 or in other memory that when executed by the processor 122, cause the processor 122 to perform the operations of the imaging device 114, the magnet device 112, and the local heating system 120. The computer code may include instructions executable with the processor 122.

The memory 130 may be any device for storing and retrieving data or any combination thereof. The memory 130 may include non-volatile and/or volatile memory, such as a random-access memory (RAM), a read-only memory (ROM), an erasable programmable read-only memory (EPROM), or flash memory. Alternatively or in addition, the memory 130 may include an optical, magnetic (hard-drive), solid-state drive or any other form of data storage device. The memory 130 may be included in any component or sub-component of the system described herein.

The user interface 132 may include any interface for displaying graphical information. The system circuitry 126 and/or the communications interface(s) may communicate signals or commands to the user interface 132 that cause the user interface 132 to display graphical information. Alternatively or in addition, the user interface 132 may be remote to the system and the system circuitry 126 and/or communication interface(s) 124 may communicate instructions, such as HTML, to the user interface 132 to cause the user interface 132 to display, compile, and/or render information content. In some examples, the content displayed by the user interface 132 may be interactive or responsive to user input. For example, the user interface 132 may communicate signals, messages, and/or information back to the communications interface or system circuitry 126.

The system may be implemented in many different ways. In some examples, the system may be implemented with one or more logical components. For example, the logical components of the system may be hardware or a combination of hardware and software. In some examples, each logic component may include an application specific integrated circuit (ASIC), a Field Programmable Gate Array (FPGA), a digital logic circuit, an analog circuit, a combination of discrete circuits, gates, or any other type of hardware or combination thereof. Alternatively or in addition, each component may include memory hardware, such as a portion of the memory 130, for example, that comprises instructions executable with the processor 122 or other processor to implement one or more of the features of the logical components. When any one of the logical components includes the portion of the memory 130 that comprises instructions executable with the processor 122, the component may or may not include the processor 122. In some examples, each logical component may just be the portion of the memory 130 or other physical memory that comprises instructions executable with the processor 122, or other processor(s), to implement the features of the corresponding component without the component including any other hardware. Because each component includes at least some hardware even when the included hardware comprises software, each component may be interchangeably referred to as a hardware component.

Some features are shown stored in a computer readable storage medium (for example, as logic implemented as computer executable instructions or as data structures in memory). All or part of the system and its logic and data structures may be stored on, distributed across, or read from one or more types of computer readable storage media. Examples of the computer readable storage medium may include a hard disk, a flash drive, a cache, volatile memory, non-volatile memory, RAM, flash memory, or any other type of computer readable storage medium or storage media. The computer readable storage medium may include any type of non-transitory computer readable medium, such as a CD-ROM, a volatile memory, a non-volatile memory, ROM, RAM, or any other suitable storage device.

The processing capability of the system may be distributed among multiple entities, such as among multiple processors and memories, optionally including multiple distributed processing systems. Parameters, databases, and other data structures may be separately stored and managed, may be incorporated into a single memory or database, may be logically and physically organized in many different ways, and may implemented with different types of data structures such as linked lists, hash tables, or implicit storage mechanisms. Logic, such as programs or circuitry, may be combined or split among multiple programs, distributed across several memories and processors, and may be implemented in a library, such as a shared library (for example, a dynamic link library (DLL).

All of the discussion, regardless of the particular implementation described, is illustrative in nature, rather than limiting. For example, although selected aspects, features, or components of the implementations are depicted as being stored in memory(s), all or part of the system or systems may be stored on, distributed across, or read from other computer readable storage media, for example, secondary storage devices such as hard disks and flash memory drives. Moreover, the various logical units, circuitry and screen display functionality is but one example of such functionality and any other configurations encompassing similar functionality are possible.

The respective logic, software or instructions for implementing the processes, methods and/or techniques discussed above may be provided on computer readable storage media. The functions, acts or tasks illustrated in the figures or described herein may be executed in response to one or more sets of logic or instructions stored in or on computer readable media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one example, the instructions are stored on a removable media device for reading by local or remote systems. In other examples, the logic or instructions are stored in a remote location for transfer through a computer network or over telephone lines. In yet other examples, the logic or instructions are stored within a given computer and/or central processing unit ("CPU").

Furthermore, although specific components are described above, methods, systems, and articles of manufacture described herein may include additional, fewer, or different components. For example, a processor 122 may be implemented as a microprocessor, microcontroller, application specific integrated circuit (ASIC), discrete logic, or a combination of other type of circuits or logic. Similarly, memories may be DRAM, SRAM, Flash or any other type of memory. Flags, data, databases, tables, entities, and other data structures may be separately stored and managed, may be incorporated into a single memory or database, may be distributed, or may be logically and physically organized in many different ways. The components may operate independently or be part of a same apparatus executing a same program or different programs. The components may be resident on separate hardware, such as separate removable circuit boards, or share common hardware, such as a same memory and processor for implementing instructions from the memory 130. Programs may be parts of a single program, separate programs, or distributed across several memories and processors.

In certain circumstances, the processor 122 may enable the robot control system 100 to be remotely operated. For instance, the processor 122 may provide teleoperative capabilities. In a specific example, the input interface 128 of the robot control system 100 may include a way to accept inputs and/or instructions from a user. As a non-limiting example, the input interface 128 may include a joystick or other such human-robot interaction devices. For instance, the user may provide inputs via the input interface 128 while visually monitoring a status of the robot control system 100, a status of the microrobot R, and/or the status of a patient via the user interface 132. Provided as non-limiting examples, the teleoperative capabilities may include adjusting the magnet device 112, the imaging device 114, and/or the local heating system 120 along each of the x-axis X, the y-axis Y, and the z-axis Z. The teleoperative capabilities may further include engaging, disengaging, and/or adjusting individual parameters of the magnet device 112, the imaging device 114, and/or the local heating system 120. One skilled in the art may select other suitable ways for enabling the robot control system 100 to be remotely operated, within the scope of the present disclosure.

The robot control system 100 may be used in various ways. For instance, as shown in FIG. 4, the robot control system 100 may be used according to a method. The method may include a step of providing the robot control system 100 having a gantry frame 102 including an x-axis guide 104, a y-axis guide 106, a first arm 108, and a second arm 110. The y-axis guide 106 may be coupled to the x-axis guide 104. Each of the first arm 108 and the second arm 110 may be coupled to the y-axis guide 106. The first arm 108 and/or the second arm 110 may be movable along a z-axis Z. A magnet device 112 may be coupled to the first arm 108. An imaging device 114 may be coupled to the second arm 110. A path for directing the robot R to a predetermined location may be determined by a processor 122. Next, a magnetic field may be applied to the robot R via the magnetic device 112. Afterwards, the method may include a step of imaging the robot via the imaging device 114. In certain circumstances, the method may include a step of heating the robot with a local heating system 120 coupled to the second arm 110. In another specific example, the method may include a step of adjusting the imaging device 114 along at least one of an x-axis X, a y-axis Y, and a z-axis Z via the processor 122. The method may also include a step of adjusting the magnetic device 112 along at least one of an x-axis X, a y-axis Y, and a z-axis Z via the processor 122. Next, a location and/or a position of the robot R may be tracked in real time via the processor 122. A skilled artisan may select other suitable ways for using the robot control system 100, within the scope of the present disclosure. It is contemplated that the order of the steps of the method may be rearranged.

Advantageously, the robot control system 100 may have the capability of autonomous microrobot adaptation, path planning and magnetic navigation to a target location, and real-time tracking in a variety of scenarios including, but not limited to, the inside of a uterus and fallopian tube phantom and with ex vivo or in vivo animal models or humans.

Example embodiments are provided so that this disclosure will be thorough and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms, and that neither should be construed to limit the scope of the disclosure. In some example embodiments, well-known processes, well-known device structures, and well-known technologies are not described in detail. Equivalent changes, modifications and variations of some embodiments, materials, compositions, and methods can be made within the scope of the present technology, with substantially similar results.

What is claimed is:

1. A robot control system configured to control a robot, comprising:

a gantry frame including an x-axis guide, a y-axis guide, a first arm, and a second arm, wherein the y-axis guide is coupled to the x-axis guide, each of the first arm and the second arm are coupled to the y-axis guide, at least one of the first arm and the second arm are movable along a z-axis;

a magnet device coupled to the first arm and configured to apply a magnetic field to the robot to magnetically actuate the robot;

an imaging device coupled to the second arm and configured to generate real-time images of the robot while the magnetic field is applied to the robot; and a processor configured to control the magnet device based at least in part on image data generated by the imaging device to control movement of the robot.

2. The robot control system of claim 1, wherein both of the first arm and the second arm are independently movable along the z-axis.

3. The robot control system of claim 1, wherein imaging device is an imaging ultrasound transducer.

4. The robot control system of claim 3, wherein the imaging device is a linear array ultrasound transducer with a frequency range of around 22 HHz to around 55 HHz and a central frequency of around 40 MHz.

5. The robot control system of claim 1, wherein magnet device includes a rotating permanent magnet to selectively provide a rotating magnetic field.

6. The robot control system of claim 5, wherein the magnet device selectively produces the rotating magnetic field up to around 500 Hz.

7. The robot control system of claim 5, wherein the magnet device includes a steering motor to direct an axis of the rotating magnetic field.

8. The robot control system of claim 1, wherein the second arm includes a local heating system.

9. The robot control system of claim 8, wherein the local heating system includes a focused ultrasound probe.

10. The robot control system of claim 1, further comprising a processor.

11. The robot control system of claim 10, wherein processor autonomously adjusts at least one of the imaging device and the magnet device along an x-axis, a y-axis, and the z-axis.

12. The robot control system of claim 10, wherein the processor autonomously plans a path for directing the robot to a predetermined location.

13. The robot control system of claim 10, wherein the processor tracks at least one of a position and a location of the robot in real time.

14. The robot control system of claim 10, wherein the processor enables teleoperative control of the robot control system.

15. A method of using a robot control system to control a robot, the method comprising the steps of:

providing the robot control system having a gantry frame including an x-axis guide, a y-axis guide, a first arm, and a second arm, the y-axis guide is coupled to the x-axis guide, each of the first arm and the second arm are coupled to the y-axis guide, at least one of the first arm and the second arm are movable along a z-axis, a magnet device coupled to the first arm, and an imaging device coupled to the second arm;

providing the robot;

applying a magnetic field to the robot via the magnetic device to magnetically actuate the robot;

imaging the robot via the imaging device while applying the magnetic field to the robot; and controlling application of the magnetic field based at least in part on image data generated by the imaging device to control movement of the robot.

16. The method of claim 15, further comprising a step of heating the robot with a local heating system coupled to the second arm.

17. The method of claim 15, further comprising a step of adjusting the imaging device along at least one of an x-axis, a y-axis, and a z-axis via a processor.

18. The method of claim 15, further comprising a step of adjusting the magnetic device along at least one of an x-axis, a y-axis, and a z-axis via a processor.

19. The method of claim 15, further comprising a step of tracking at least one of a location and a position of the robot via a processor.

20. The method of claim 15, further comprising a step of determining a path for directing the robot to a predetermined location.

* * * * *